United States Patent
Kang et al.

[11] Patent Number: 6,146,898
[45] Date of Patent: Nov. 14, 2000

[54] APPARATUS AND METHOD FOR ON-LINE DECOMPOSITION OF HYDROGEN PEROXIDE SOLUTION IN FABRICATION OF SEMICONDUCTOR DEVICE

[75] Inventors: Sung-chul Kang, Songnam; Dong-soo Lee, Seoul, both of Rep. of Korea

[73] Assignee: Samsung Electronics Co., Ltd., Suwon, Rep. of Korea

[21] Appl. No.: 09/157,945

[22] Filed: Sep. 22, 1998

Related U.S. Application Data

[62] Division of application No. 08/842,503, Apr. 24, 1997, Pat. No. 5,939,032.

[30] Foreign Application Priority Data

Jun. 20, 1996 [KR] Rep. of Korea ............... 96-22656

[51] Int. Cl.[7] ........................................ G01N 33/20
[52] U.S. Cl. ........................ 436/73; 436/79; 436/80; 436/81; 436/82; 436/83; 436/84; 436/135; 436/159; 436/175; 436/181
[58] Field of Search ................... 436/73, 79–84, 436/135, 155, 159, 175, 181; 422/136, 211, 239, 312; 210/500.21, 500.23

[56] References Cited

U.S. PATENT DOCUMENTS

| | | | |
|---|---|---|---|
| 3,894,538 | 7/1975 | Richter | 128/260 |
| 3,912,451 | 10/1975 | Gaglia, Jr. | 134/42 X |
| 3,996,141 | 12/1976 | Updike | 210/501 |
| 4,279,883 | 7/1981 | Izumi et al. | 423/584 |
| 4,601,884 | 7/1986 | Coeckelberghs et al. | 422/113 |
| 4,750,610 | 6/1988 | Ryder | 206/5.1 |
| 4,792,435 | 12/1988 | Nakajima | 422/110 |
| 5,227,042 | 7/1993 | Zawodzinski et al. | 204/403 |
| 5,292,515 | 3/1994 | Moro et al. | 424/422 |
| 5,536,241 | 7/1996 | Zapol | 604/23 |
| 5,711,146 | 1/1998 | Armstrong et al. | 60/218 |

FOREIGN PATENT DOCUMENTS 2273773  6/1994  United Kingdom.

OTHER PUBLICATIONS

M. V. Twigg "Catalyst Handbook" 1989, Wolfe Publishing Ltd. pp. 34–35.
M. Aoyagi et al. Chem. Abstr. 1991, 114, 220331w, Jun. 1991.
H. S. Folger "Elements of Chemical Reaction Engineering" 1992, Prentice Hall Inc. pp. 163–165.

*Primary Examiner*—Arlen Soderquist
*Attorney, Agent, or Firm*—Jones Volentine, LLC

[57] ABSTRACT

An apparatus and method for on-line decomposition of a hydrogen peroxide solution, for use in fabricating a semiconductor device, includes a membrane tube having a porous plug inserted in each end, with the porous plugs defining a space where a platinum catalyst is disposed. A first coupling tube is inserted into one end of the membrane tube to supply a hydrogen peroxide sample to the membrane tube. The hydrogen peroxide contained in hydrogen peroxide sample is decomposed into water and oxygen gas according to an action of the platinum catalyst. A second coupling tube is inserted into a second end of the membrane tube to discharge a diluted hydrogen peroxide solution to an analytical instrument, where the decomposed hydrogen peroxide solution is analyzed on-line.

5 Claims, 1 Drawing Sheet

APPARATUS AND METHOD FOR ON-LINE DECOMPOSITION OF HYDROGEN PEROXIDE SOLUTION IN FABRICATION OF SEMICONDUCTOR DEVICE

CROSS REFERENCE TO RELATED APPLICATIONS

This is a divisional application of application Ser. No. 08/842,503, filed Apr. 24, 1997, now issued as U.S. Pat. No. 5,939,032, on Aug. 17, 1999.

BACKGROUND OF THE INVENTION

1. Field of the Invention

The present invention relates to an apparatus and a method for on-line decomposition of a hydrogen peroxide solution for use in the fabrication of a semiconductor device and, more particularly, to an apparatus and a method for decomposing the hydrogen peroxide solution on-line and then injecting the decomposed products into an analytical instrument to thereby analyze the micro contaminants in the hydrogen peroxide solution.

2. Discussion of the Related Art

As the size of a semiconductor device is reduced further and further, and thus becomes more densely integrated, micro contaminants existing in the constituent layers of the semiconductor device exhibit a greater effect on the device characteristics. Consequently, there is a continuing emphasis to remove the micro contaminants throughout the fabrication process of the semiconductor device.

Generally, a wet cleaning process is the most widely used procedure to reduce or eliminate semiconductor wafer contamination. However, the chemicals used in the wet cleaning process must also have a high degree of purity so as to prevent a wafer from being re-contaminated by the wet cleaning process itself. Therefore, it is necessary to perform a quantitative and qualitative analysis of the micro contaminants contained in the chemicals prior to their use. The micro contaminants can include heavy metals such as iron (Fe), aluminum (Al), copper (Cu), and the like, and ions of sodium ($Na^+$), ammonium ($NH_4^+$), nitrate ($NO_3^-$), chloride ($Cl^-$), and the like. In order to analyze these contaminants, analytical apparatus and methods are used, for example, a graphite reactor atomic absorption spectrometer (GFAAS), an induced coupling plasma mass spectroscope (ICP-MS) and an ion-exchange chromatograpy (IC).

Hydrogen peroxide solution is one chemical that is widely used in wet cleaning processes for semiconductor devices. However, the hydrogen peroxide readily oxidizes, making it difficult for the analyzer to perform a successful analysis because the oxidation may cause damage to the analytical instruments. In addition, the oxidation could also result in changes in viscosity of the cleaning solution, and the generation of bubbles when analyzing a highly concentrated hydrogen peroxide solution in the above analytical instruments.

Accordingly, to perform an efficient analysis of the hydrogen peroxide solution in an analytical instrument, it is necessary to reduce the concentration of hydrogen peroxide. Different methods are used to reduce the concentration of the hydrogen peroxide. In a so-called dilution method, the hydrogen peroxide solution is diluted with distilled water. In another so-called decomposition method, the hydrogen peroxide contained in the hydrogen peroxide solution is decomposed into water and oxygen gas.

The dilution method is easy and simple to carry out, but it has a disadvantage in that the detection capacity of the instrument may deteriorate as a result of the frequent dilution of the sample. Accordingly, it is not suitable for a method of reducing the concentration of hydrogen peroxide which requires a detection capacity for contaminants on the order of a hundred parts per trillion (ppt) and less.

In an attempt to solve this problem, another technique has been developed whereby the hydrogen peroxide solution is concentrated in an analytical column before an analysis is carried out. In this technique, the hydrogen peroxide solution is first diluted to a designated point so that it does not damage the analytical column, and is then again concentrated on line in the column so as to minimize the deterioration of detection sensitivity. But, this method is not applicable to performing infinitesimal quantitative analysis because it requires another apparatus and additional concentration steps. As a result, the analysis time is prolonged and the possible contamination of the sample is increased due to the extended sample flow path.

On the other hand, a decomposition method, which is carried out using a platinum catalyst, has merit in that the detection capacity is not lowered because there is no need to dilute the sample. In such a platinum catalyst decomposition method, a platinum wire or platinum net is used as a heterogeneous catalyst in the hydrogen peroxide solution. The platinum catalyst can be reused because the catalyst does not dissolve in the hydrogen peroxide solution, and an aqueous solution is produced according to the decomposition of hydrogen peroxide.

However, this method also suffers some drawbacks in that it takes a long time to decompose the sample, raising other possible contamination problems during the decomposition. Also, the contaminants contained within the sample may be chemically changed due to the heat generated by the decomposition of the hydrogen peroxide solution.

In another decomposition method for hydrogen peroxide using ultraviolet (UV) rays, the hydrogen peroxide solution contained in a quartz container is irradiated by the ultraviolet (UV) rays. One benefit of the UV method is that there is no need to add any materials to the hydrogen peroxide solution. However, the UV method also presents problems, perhaps more serious than the platinum catalyst decomposition method, in that it takes a much longer time for decomposition and causes much greater chemical changes in the contaminants in the solution.

An additional disadvantage of both of the above-described platinum catalyst and UV decomposition methods is that each is carried out in a batch process, and therefore the apparatus for decomposition cannot be connected on-line to the analytical instruments. As such, it is difficult to perform an on-line, real-time automatic analysis of the sample.

Accordingly, a need exists for an on-line decomposition apparatus and method for reducing the concentration of hydrogen peroxide contained in the hydrogen peroxide solution so as to perform an on-line, real-time automatic analysis of micro contaminants in an analytical instrument.

SUMMARY OF THE INVENTION

Accordingly, the present invention is directed to an apparatus and method for on-line decomposition of a hydrogen peroxide solution for use in the fabrication of semiconductor device that substantially overcomes one or more of the problems due to limitations and disadvantages of the related art.

An object of the present invention is to provide an apparatus for on-line decomposition of a hydrogen peroxide solution for use in the fabrication of semiconductor device, which reduces the concentration of hydrogen peroxide contained in the hydrogen peroxide solution so as allow for an on-line real time automatic analysis of micro contaminants in an analytical instrument.

Another object of the present invention is to provide a method of on-line decomposition of hydrogen peroxide solution using the above apparatus.

To achieve these and other advantages and in accordance with the purpose of the present invention, as embodied and broadly described, there is provided an apparatus for on-line decomposition of a hydrogen peroxide solution for use in fabricating a semiconductor device, comprising: a membrane tube having first and second ends; a porous plug inserted in each of the first and second ends, the porous plugs being separated by a designated distance, thereby defining a space within the membrane tube; a platinum catalyst disposed in the space within the membrane tube; an outer glass tube enclosing the membrane tube; a first coupling tube inserted into the first end of the membrane tube so as to supply a hydrogen peroxide sample to the membrane tube; and a second coupling tube inserted into the second end of the membrane tube so as to discharge a decomposed hydrogen peroxide solution which passes through the platinum catalyst disposed in the membrane tube, said decomposed hydrogen peroxide solution being analyzed on-line.

The first coupling tube is connected to a sample-supply pump for pumping the sample from a sample container and thereafter supplying the sample through the first coupling tube, so as to make it easy to supply the sample.

The membrane tube, which is permeable to gas and impermeable to liquid, may be made of porous poly tetrafluoroethylene (PTFE), porous poly vinylidenefluoride (PVDF), or porous poly propylene (PP). The porous plugs for fixing the platinum catalyst inside the membrane tube may be made of TEFLON™ or poly propylene. The first and second coupling tubes may also be made of TEFLON™ materials One end of the outer glass tube is closed in relation to the membrane tube and the other end of the outer glass tube is opened in relation to the membrane tube, so that it is easy for the water vapor and the oxygen gas generated during the decomposition of hydrogen peroxide solution to exit to the atmosphere via the open end.

The platinum catalyst may take on many forms, including platinum powder, a platinum-coated glass bead, a platinum-coated silica gel, a highly pure platinum wire, a platinum-coated nichrome wire, and 5% platinum active carbon powder.

In another aspect, the present invention provides for a method of on-line decomposition of hydrogen peroxide solution for use in fabricating a semiconductor device, said method comprising the steps of: supplying a sample of hydrogen peroxide solution, from a sample container via a first coupling tube, to a membrane tube having a platinum catalyst disposed therein; decomposing hydrogen peroxide contained in the hydrogen peroxide solution into water and oxygen gas according to an action of the platinum catalyst; injecting the decomposed hydrogen peroxide solution from the membrane tube into an analytical instrument via a sample injector; and analyzing the decomposed hydrogen peroxide solution on-line.

The oxygen gas generated as a result of decomposition of the hydrogen peroxide solution is immediately discharged through the membrane tube, so that the concentration of hydrogen peroxide in the hydrogen peroxide solution can be reduced. An on-line automatic analysis is carried out when the decomposed sample is injected into the analytical instrument.

It is to be understood that both the foregoing general description and the following detailed description are exemplary and explanatory and are intended to provide further explanation of the invention as claimed.

BRIEF DESCRIPTION OF THE ATTACHED DRAWINGS

The foregoing and other objects, aspects and advantages will be better understood from the following detailed description of a preferred embodiment of the invention with reference to the drawings, in which:

FIG. 1 is a sectional view showing an apparatus for on-line decomposition of a hydrogen peroxide solution according to an embodiment of the present invention; and FIG. 2 is a schematic view of the on-line connection of the apparatus in FIG. 1 between a sample container and an analytical instrument.

DETAILED DESCRIPTION OF A PREFERRED EMBODIMENT OF THE INVENTION

Reference will now be made in detail to a preferred embodiment of the present invention, examples of which are illustrated in the accompanying drawings.

Figure 1:
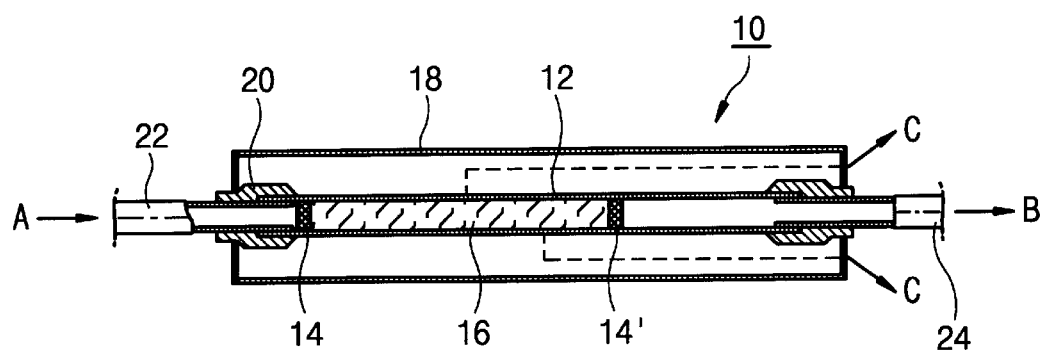
Figure 2:
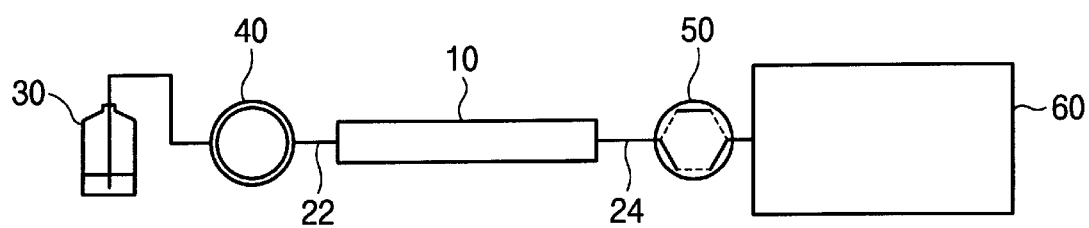

Referring to FIGS. 1 and 2, the on-line decomposition apparatus 10 includes a first coupling tube 22 connected at one end to a sample-supply pump 40, with the other end of the first coupling tube 22 being inserted into one end of a membrane tube 12 contained within the apparatus 10. TEFLON™ tape is used to seal the connection between the first coupling tube 22 and the membrane tube 12. When TEFLON™ is used in this specification, it refers to a commercially-available type of the polymer tetrafluoroethelyne. However, any substance exhibiting similar properties, such as a porous poly tetrafluoroethelyne (PTFE), a porous poly vinylidenefluoride (PVDF), or porous poly propylene (PP) may be used in place of TEFLON™.

A second coupling tube 24 is connected at one end to a sample injector 50, with the other end of the second coupling tube 24 being inserted into a second end of the membrane tube 12 contained within the apparatus 10. TEFLON™ tape is used to seal the connection between the second coupling tube 24 and the membrane tube 12. The first and second coupling tubes 22, 24 may be made of teflon, for example.

At the locations on the inside of the membrane tube 12 where the first and second coupling tubes 22, 24 are inserted, plugs 14, 14' are provided. The plugs 14, 14' are in the form of disks which are made of porous polymer materials such as TEFLON™ or poly propylene, for example. A platinum catalyst 16 is disposed between the two plugs 14, 14'.

The membrane tube 12 is enclosed by a glass tube 18 having a larger diameter so as to exclude possible contamination from the outside air. The end of the glass tube 18 closest to the sample-supply pump 40 contacts and closes around the membrane tube 12, while the other end of the glass tube 18 closest to the sample injector 50 is opened, that is, it does not contact the membrane tube 12, so as to allow gas from the inside of the membrane tube 12 to effuse to the outside.

As shown in FIG. 2, in the apparatus for on-line decomposition of hydrogen peroxide solution according to the present invention, the first coupling tube 22 is connected to a sample container 30 through the sample-supply pump 40 and to an analytical instrument 60 through the sample injector 50. In a preferred embodiment of the present invention, the analytical instrument used is an ion-exchange chromatography (IC), for example, Model No. ASRS-I made by Dionex Co. of Sunnyvale, Calif.

The membrane tube 12 is preferably made of porous TEFLON™ materials, which makes it possible to change the length of the tube. Also, the porous TEFLON™ materials allow the membrane tube 12 to separate gas from liquid because the TEFLON™ materials allow gas to flow in and out but they prevent liquid from being transmitted. In other words, the membrane tube 12 is permeable to gas and impermeable to liquid. More particularly, the membrane tube 12 may be made of, for example, any of the following: porous poly tetrafluoroethylene (PTFE), porous poly vinylidene fluoride (PVDF) or porous poly propylene (PP).

The platinum catalyst 16 in the membrane tube 12 may be, for example, a platinum powder, a highly pure platinum wire, a platinum-coated nichrome wire, a platinum-coated glass bead, a platinum-coated silica gel, or similar material.

The apparatus and method for on-line decomposition of a hydrogen peroxide solution according to the present invention operates as follows. The hydrogen peroxide solution is pumped by the sample-supply pump 40 from the sample container 30 through the first coupling tube 22, through the porous plug 14, and then into the membrane tube 12 (in the direction of A in FIG. 1). Hydrogen peroxide contained in the hydrogen peroxide solution undergoes a rapid decomposition into water and oxygen gas by the action of the platinum catalyst 16 when passing through the membrane tube 12, so that the hydrogen peroxide solution is diluted. During this process, the oxygen gas that is generated by the decomposition passes through the porous membrane tube 12 and is discharged into the air through the open end of the glass tube 18 (in the direction of C in FIG. 1). Then, the decomposed or diluted hydrogen peroxide solution is injected into the analytical instrument through the sample injector 50 (in the direction of B in FIG. 1) for an on-line, real-time analysis.

A performance test was carried out in the apparatus for on-line decomposition of hydrogen peroxide solution according to the present invention, where platinum catalysts 16 of various forms were disposed in the membrane tube 12 thereof. For the test, the first coupling tube 22 was connected to the membrane tube 12 and to the peristaltic sample-supply pump 40. A concentrated hydrogen peroxide solution was then injected into the on-line decomposition apparatus. The resulting solution was collected and the remaining hydrogen peroxide which was not decomposed was titrated with $KMnO_4$ so as to measure the decomposition degree. The results are shown in Table 1.

TABLE 1

Performance Test Using Different Platinum Catalysts

| Forms of Platinum Catalyst | Flux Velocity (mL/min) | Decomposition Degree |
|---|---|---|
| Screw-Shaped Platinum Wire | 0.69 | 46.0 |
| Platinum-Coated Glass Beads | 0.20 | 65.3 |
| 5% Platinum Active Carbon Powder | 0.20 | >99.9 |
| Platinum-Plated Nichrome Wire | 0.21 | >99.9 |
| Platinum Wire | 0.29 | 99.6 |

As shown in Table 1, the decomposition degree is strongly affected by the materials and the forms of the platinum catalyst employed. In particular, the 5% platinum active carbon powder, the platinum-plated nichrome wire and the platinum wire all achieve a high decomposition degree.

According to the present invention, many samples of hydrogen peroxide can be rapidly processed as a result of the automated, real-time, on-line decomposition apparatus and method. In addition, the stability and reliability of wet cleaning processes are ensured since the purity of the hydrogen peroxide solution is immediately certified and the efficiency in quality control of chemicals is promoted.

It will be apparent to those skilled in the art that various modifications and variations can be made in the apparatus and method described above without departing from the spirit or scope of the invention. Thus, it is intended that the present invention cover the modifications and variations of this invention that come within the scope of the appended claims and their equivalents.

What is claimed is:

1. A method of on-line decomposition of a hydrogen peroxide solution for use in fabricating a semiconductor device, said method comprising the steps of:

supplying a sample of hydrogen peroxide solution, from a sample container via a first coupling tube, to a membrane tube having a platinum catalyst disposed therein;

decomposing hydrogen peroxide contained in said hydrogen peroxide solution into water and oxygen gas according to an action of said platinum catalyst;

injecting said decomposed hydrogen peroxide solution from said membrane tube into an analytical instrument via a sample injector;

analyzing said decomposed hydrogen peroxide solution on-line; and allowing the oxygen gas generated during the decomposing step to flow into the atmosphere.

2. The method as defined in claim 1, wherein said decomposing step is carried out on-line will said hydrogen peroxide solution is being supplied to a wet cleaning process used in fabricating the semiconductor device.

3. The method as defined in claim 1, wherein said decomposing step is carried out using a platinum catalyst selected from the group consisting of platinum powder, a platinum-coated glass bead, and a platinum-coated silica gel.

4. The method as defined in claim 1, wherein said decomposing step is carried out using a platinum catalyst selected from the group consisting of a highly pure platinum wire, a platinum-coated nichrome wire, and 5% platinum active carbon powder.

5. The method as defined in claim 1, wherein micro contaminants contained in said decomposed hydrogen peroxide are analyzed in said analyzing step.

* * * * *